United States Patent
Ideker et al.

(10) Patent No.: US 6,205,357 B1
(45) Date of Patent: Mar. 20, 2001

(54) METHODS AND APPARATUS FOR DETECTING AND TREATING MEDICAL CONDITIONS OF THE HEART

(75) Inventors: Raymond E. Ideker, Birmingham, AL (US); Jay A. Warren, North Oaks; Bruce H. KenKnight, Maple Grove, both of MN (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/206,022

(22) Filed: Dec. 4, 1998

(51) Int. Cl.$^7$ ........................................ A61N 1/39
(52) U.S. Cl. ................................ 607/14; 607/15
(58) Field of Search ..................... 607/14, 15, 5

(56) References Cited

U.S. PATENT DOCUMENTS

| | | |
|---|---|---|
| 4,375,817 | 3/1983 | Engle et al. . |
| 4,572,192 | 2/1986 | Jackman et al. . |
| 4,750,494 * | 6/1988 | King . |
| 4,754,753 | 7/1988 | King . |
| 4,869,252 | 9/1989 | Gilli . |
| 5,042,497 * | 8/1991 | Shapland . |
| 5,184,616 | 2/1993 | Weiss . |
| 5,191,884 | 3/1993 | Gilli et al. . |
| 5,205,283 | 4/1993 | Olson . |
| 5,215,083 | 6/1993 | Drane et al. . |
| 5,350,401 | 9/1994 | Levine . |
| 5,366,486 | 11/1994 | Zipes et al. . |

(List continued on next page.)

FOREIGN PATENT DOCUMENTS

| | | |
|---|---|---|
| 0 575 674 A1 | 12/1993 | (EP) . |
| 0 830 876 A2 | 3/1998 | (EP) . |
| WO 98/25670 | 6/1998 | (WO) . |

OTHER PUBLICATIONS

International Search Report PCT/US99/14612; dated Oct. 25, 1999.

Raymond E. Ideker and Bruce H. KenKnight, Ser. No. 09/153,407 filed Sep. 15, 1998 entitled *Methods and Apparatus for Detecting Medical Conditions of the Heart*.

*Primary Examiner*—Carl H. Layno
(74) *Attorney, Agent, or Firm*—Myers Bigel Sibley & Sajovec

(57) ABSTRACT

An implantable system for detecting electrical activity from a patient's heart comprises a first sensing electrode configured for positioning through the coronary sinus ostium and within a vein on the left surface of the left ventricle of the heart for sensing electrical activity from the heart, and a detector operatively associated with the first sensing electrode for determining (e.g., diagnosing or prognosing) a medical condition of the heart with the sensed electrical activity. Typically the system further comprises a second sensing electrode configured for positioning in the right ventricle of the heart, where the detector is operatively associated with both the first sensing electrode and the second sensing electrode. The second sensing electrode may be positioned in other locations as well, such as also within a vein on the left surface of the left ventricle of the heart (although spaced apart from the first sensing electrode), in the right atrium, in the superior vena cava, etc. Finally, a third sensing electrode may also be included, with the third electrode positioned in any of the foregoing locations (again, spaced apart from the first and second electrodes), with the detector operatively associated with all of the first, second, and third sensing electrodes. Determination of a medical condition may be carried out by any suitable means, such as by detecting premature beats in the heart. The method is particularly useful for identifying the chamber of premature beat origin.

32 Claims, 7 Drawing Sheets

U.S. PATENT DOCUMENTS

| | | | |
|---|---|---|---|
| 5,425,749 | * | 6/1995 | Adams ................................... 607/5 |
| 5,447,519 | | 9/1995 | Peterson . |
| 5,458,619 | | 10/1995 | Olson . |
| 5,464,429 | | 11/1995 | Hedberg et al. . |
| 5,464,430 | | 11/1995 | Rossing . |
| 5,545,183 | | 8/1996 | Altman . |
| 5,549,641 | | 8/1996 | Ayers et al. ............................ 607/4 |
| 5,571,142 | * | 11/1996 | Brown et al. ........................... 607/5 |
| 5,607,385 | | 3/1997 | Francischelli et al. . |
| 5,814,079 | | 9/1998 | Kieval . |
| 5,951,593 | * | 9/1999 | Lu et al. . |
| 6,058,328 | * | 5/2000 | Levine et al. . |

\* cited by examiner

METHODS AND APPARATUS FOR DETECTING AND TREATING MEDICAL CONDITIONS OF THE HEART

FIELD OF THE INVENTION

The present invention concerns methods and apparatus for preventing atrial and/or ventricular arrhythmia prior to occurrence thereof, and treating such arrhythmia if it should occur.

BACKGROUND OF THE INVENTION

Atrial fibrillation is one of the most common cardiac arrhythmia. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility.

Unlike patients afflicted with ventricular fibrillation, patients afflicted with atrial fibrillation are conscious. The pain associated with the administration of the defibrillation shock can be severe, and there is a need for means of carrying out atrial defibrillation in a manner that is less painful to the patient being treated.

Numerous patients are afflicted with both atrial and ventricular arrrhythmias. For such patients, it would be desirable to provide a single device that can carry out both atrial and ventricular defibrillation with minimum shock strength, and with minimal surgical intervention.

U.S. Pat. No. 5,549,641 to Ayers et al., issued Aug. 27, 1996, describes an atrial cardioverter and method in which atrial arrhythmia is first detected. If no arrhythmia is detected, then no action is taken. If arrhythmia is detected, the system proceeds through determining whether the arrhythmia is an atrial flutter, or a more severe arrhythmia, and a therapeutic pulse ranging from pace pulses or low energy cardioversion through intermediate and high energy cardioversion is given. A disadvantage of this system is that it is not capable of preventing an arrhythmia prior to occurrence thereof. Other systems which provide different levels of therapeutic pulses, but only after the onset of an arrhythmia, are described in U.S. Pat. No. 4,375,817 to Engle et al., U.S. Pat. No. 4,869,252 to Gilli, and U.S. Pat. No. 5,350,401 to Levine.

A problem with the aforesaid devices is that therapy begins only after the onset of arrhythmia. It would be preferable to have a device that incorporated prognostic features and preventive therapy to prevent arrhythmia from initiating, and, if arrhythmia should initiate, to promptly treat the arrhythmia.

SUMMARY OF THE INVENTION

A first aspect of the invention is a method of selecting a cardiac therapy to be delivered to a patient's heart for the prevention or treatment of cardiac arrhythmia by an implantable system. The method comprises detecting electrical activity from the heart of the patient, predicting the future onset of a cardiac arrhythmia in the patient from the detected electrical activity (i.e., before the arrhythmia actually occurs), and then delivering a first therapeutic electrical pulse to the heart of the patient prior to the onset of cardiac arrhythmia. The arrhythmia monitored for may be an atrial arrhythmia, a ventricular arrhythmia, or both. After the first therapeutic electrical pulse is delivered, the effectiveness of that pulse in preventing cardiac arrhythmia is then monitored from the detected electrical activity. A second therapeutic electrical pulse is then delivered to the heart of the patient at the onset of the cardiac arrhythmia if the first therapeutic electrical pulse is not effective. In a preferred embodiment, the step of delivering a second therapeutic electrical pulse is followed by the steps of: monitoring the effectiveness of the second therapeutic electrical pulse in treating the cardiac arrhythmia, and then delivering a third therapeutic electrical pulse to the heart of the patient if the second therapeutic electrical pulse is not effective in treating the arrhythmia. The third therapeutic electrical pulse is a higher energy pulse than the second therapeutic electrical pulse.

Systems for carrying out such methods are described in detail below. In a preferred embodiment, the system of the invention comprises a first sensing electrode configured for positioning through the coronary sinus ostium and within a vein on the left surface of the left ventricle of the heart for sensing electrical activity from the heart, and a detector operatively associated with the first sensing electrode for determining (e.g., diagnosing or prognosing) an arrhythmia with the sensed electrical activity. Typically the system further comprises a second sensing electrode configured for positioning in the right ventricle of the heart, where the detector is operatively associated with both the first sensing electrode and the second sensing electrode. The second sensing electrode may be positioned in other locations as well, such as also within a vein on the left surface of the left ventricle of the heart (although spaced apart from the first sensing electrode), in the right atrium, in the superior vena cava, etc. Finally, a third sensing electrode may also be included, with the third electrode positioned in any of the foregoing locations (again, spaced apart from the first and second electrodes), with the detector operatively associated with all of the first, second, and third sensing electrodes. Determination of a medical condition may be carried out by any suitable means, such as by detecting premature beats in the heart. This method is particularly useful for identifying the chamber of premature beat origin (e.g., left ventricle, right ventricle, left atrium, or right atrium).

The detector may be configured to detect the presence of sinus rhythm with syntactic relationships among electrogram features. The detector may be configured to predict cardiac arrhythmia in the patient prior to the onset of the cardiac arrhythmia, or the present occurrence of cardiac arrhythmia in the patient. The detector may be configured to discriminate the location of origin of premature beats in the heart (e.g., to discriminate an atrial location of origin from a ventricular location of origin of premature beats in the heart, with or without the ability to discriminate left ventricular from right ventricular locations of origin, and with or without the ability to discriminate left atrial from right atrial locations of origin).

In a particular embodiment, a method of selecting a cardiac therapy to be delivered to a patient's heart by an implantable system of the invention comprises detecting a first set of electrical activity from the heart from a first sensing electrode positioned within a vein on the surface of the left ventricle of the heart; detecting a second set of electrical activity from the heart from a second sensing electrode positioned within the right ventricle of the heart; then selecting an electrical therapy to be delivered by the implantable system based on the first and second sets of detected electrical activity; and then delivering the selected electrical therapy.

The first, second, and third therapeutic electrical pulses can be administered by any suitable means. In one embodiment, the system includes a first catheter configured for positioning in the right ventricle of the heart; a second catheter configured for positioning through the coronary sinus ostium and in the coronary sinus of the heart, with the first and second catheters together carrying at least three defibrillation electrodes. A power supply is included, a control circuit is operatively associated with the power supply and the electrodes. The control circuit is configured to deliver atrial therapeutic pulses through at least two of the electrodes, and/or ventricular therapeutic pulses through at least two of the electrodes.

The system may include a first and second pair of atrial therapeutic electrodes operatively associated with the control circuit and power supply, with the first pair of atrial therapeutic electrodes configured for delivering an atrial therapeutic pulse segment along a first current pathway and the second pair of atrial therapeutic electrodes configured for delivering a second atrial therapeutic pulse segment along a second current pathway that is different from the first current pathway, and wherein the control circuit is configured for delivering an atrial therapeutic pulse comprising in sequence the first and second atrial therapeutic pulses. The first, second, and/or third therapeutic pulses may be delivered as two segments along different current pathways.

In addition to or in the alternative to the atrial therapeutic electrodes, the system may also include a first and second pair of ventricular therapeutic electrodes operatively associated with the control circuit and the power supply, with the first pair of ventricular therapeutic electrodes configured for delivering a first ventricular therapeutic pulse segment along a first current pathway and the second pair of ventricular therapeutic electrodes configured for delivering a second therapeutic pulse segment along a second current pathway that is different from the first current pathway, and wherein the control circuit is configured for delivering a ventricular therapeutic pulse comprising in sequence the first and second ventricular therapeutic pulse segments. Again, the first, second, and/or third therapeutic pulses may be delivered as two segments along different current pathways.

The foregoing and other objects and aspects of the present invention are explained in detail in the drawings herein and the specification set forth below.

DETAILED DESCRIPTION OF THE PREFERRED EMBODIMENTS

Figure 1:
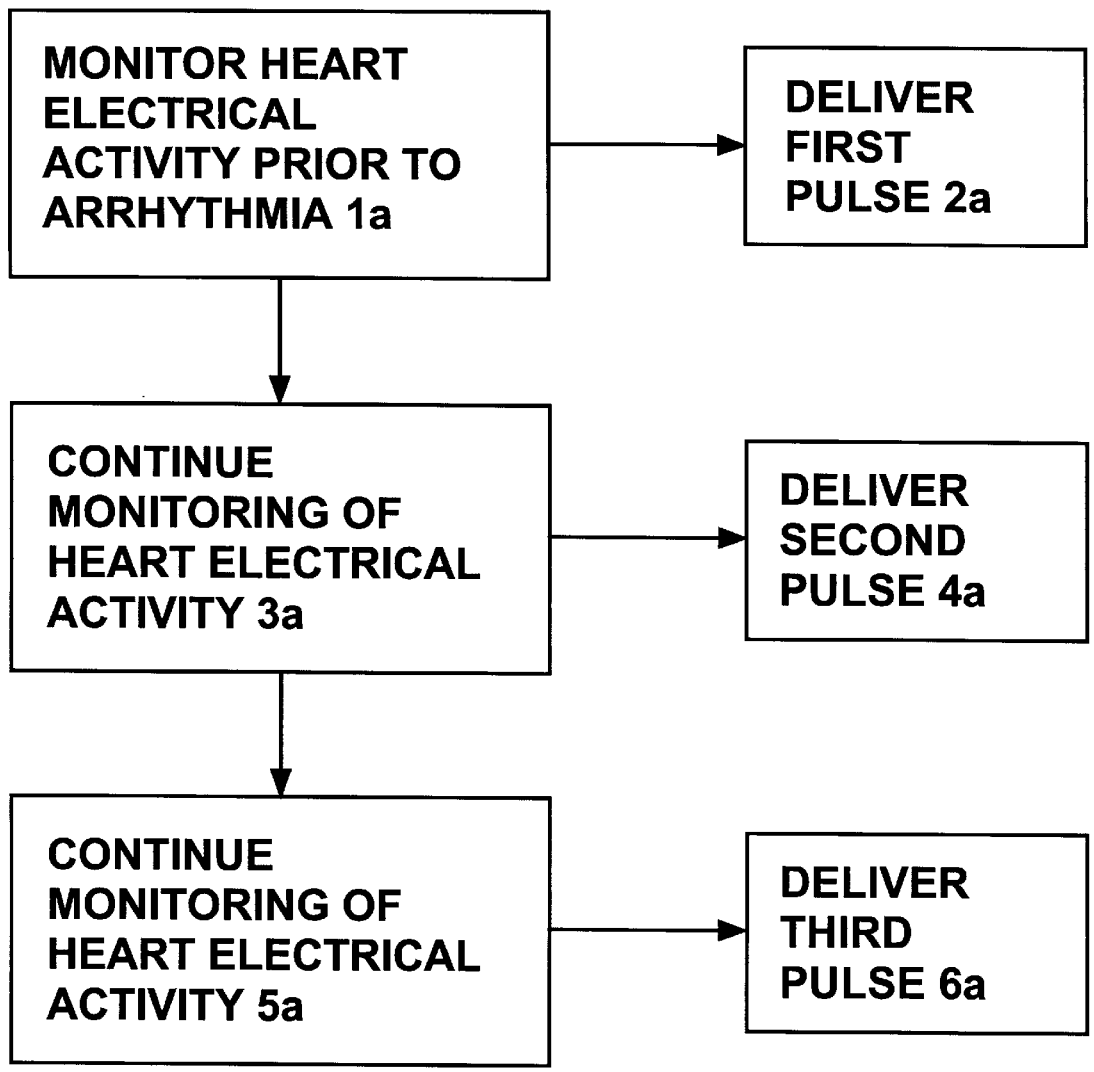
FIG. 1 schematically illustrates a method of the invention.

An implantable cardioverter/defibrillator (ICD) of the present invention includes an implantable housing that contains a hermetically sealed electronic circuit. The housing optionally, but preferably, includes an electrode comprising an active external portion of the housing, with the housing implanted in the left or right, preferably left, thoracic region of the patient (e.g., subcutaneously, in the left or right, preferably left, pectoral region) in accordance with known techniques such as described in U.S. Pat. No. 5,292,338 to Bardy.

As used herein, "means" such as detector means may be implemented as various forms of hardware, including circuits and integrated circuits, as software, and as combinations of hardware and software.

Electrodes used to carry out the present invention are typically carried by catheters or leads, which are electrically and mechanically connected to the housing through a header unit, and which are insertable into the heart (typically through the superior or inferior vena cava) without the need for surgical incision into the heart, in accordance with known techniques. The term "catheter" as used herein includes "stylet" and is also used interchangeably with the term "lead".

An electrode positioned "through the coronary sinus ostium and within a vein on the surface of the left ventricle of the heart", as that phrase is used herein, may reside in any of a variety of locations. It may be located in:

(1) the coronary sinus itself;
(2) the portion of the great cardiac vein which runs along the base plane of the heart;
(3) the portion of the great cardiac vein that extends around the heart to the point at which the great vein turns downward toward the apex of the heart;
(4) the portion of the great cardiac vein which runs between the base and apex of the heart (either including or excluding portions of (3) above);
(5) a tributary to the great cardiac vein, such as the anterior interventricular vein, the posterior cardiac vein, or the middle cardiac vein.

The therapeutic pulses may be administered in accordance with known techniques, as described in U.S. Pat. No. 5,282,837 to Adams; U.S. Pat. No. 5,433,729 to Adams et al.; U.S. Pat. No. 5,014,696 to Mehra; U.S. Pat. No. 5,099,838 to Bardy; U.S. Pat. No. 5,431,683 to Bowald et al.; U.S. Pat. No. 5,423,865 to Bowald; U.S. Pat. No. 5,690,686 to Min et al. (the disclosures of which are incorporated by reference herein in their entirety).

In addition, the electrode may be configured so that it is positioned entirely within one of the foregoing sites (see, e.g., U.S. Pat. No. 5,423,865 to Bowald et al.); or may be configured so that it is positioned in two or more adjacent sites (see, e.g., U.S. Pat. Nos. 5,014,696 to Mehra et al; 5,099,838 to Bardy; 5,193,535 to Bardy; 5,690,686 to Min et al.). For example, the electrode may be positioned: (i) in the coronary sinus and the portion of the great cardiac vein which runs along the base plane of the heart; (ii) in the portion of the great cardiac vein of the heart which runs along the base plane of the heart and the portion of the great cardiac vein that extends around the heart to the point at which the great vein turns downward toward the apex of the heart; (iii) in the portion of the great cardiac vein that extends around the heart to the point at which the great vein turns downward toward the apex of the heart and the portion of the great cardiac vein which runs between the base and apex of the heart; etc. Where the electrode is a sensing electrode, configurations that position all, or a portion of, the electrode in the coronary sinus are less preferred, and configurations that position the electrode in one or more of locations 3–5 above are more preferred.

Electrodes used to carry out the present invention, including both stimulation electrodes and sensing electrodes, may be of any suitable construction. For example, the electrodes may be rigid, hollow cylindrical electrodes electrodes which are fixed by radial expansion to a blood vessel wall and through which blood may flow, or the electrodes may be solid electrodes (i.e., solid with respect to blood flow) carried by a flexible lead, which lead is sufficiently rigid to maintains the desired position of the electrode in a blood vessel. Where a solid electrode is employed, blood may or may not flow around the electrode, as discussed below.

The method of the invention is presented in schematic overview in FIG. 1. The method comprises first detecting electrical activity from the heart of the patient, predicting the future onset of a cardiac arrhythmia in the patient from the detected electrical activity (i.e., before the arrhythmia actually occurs), schematically depicted as block 1a. If predicted, a first therapeutic electrical pulse is delivered to the heart of the patient prior to the onset of cardiac arrhythmia 2a. The arrhythmia monitored for may be an atrial arrhythmia, a ventricular arrhythmia, or both. After the first therapeutic electrical pulse is delivered, the effectiveness of that pulse in preventing cardiac arrhythmia is then monitored from the detected electrical activity 3a. A second therapeutic electrical pulse 4a is then delivered to the heart of the patient at the onset of the cardiac arrhythmia if the first therapeutic electrical pulse is not effective. The second therapeutic electrical pulse can be a higher energy pulse than the first therapeutic electrical pulse, can be a different wave form, and/or can be across a different current path. Advantageously, the therapy circuit employed in carrying out the method (see FIG. 6) can include a storage capacitor for delivering the electrical energy for the second therapeutic pulse, and charging of the storage capacitor can be initiated after the arrhythmia is predicted but before the first therapeutic pulse, after the first therapeutic pulse, during subsequent monitoring of the efficacy of the first therapeutic pulse, or combinations thereof. In this manner, the second therapeutic pulse can be delivered promptly, within the first two, three or four beats after the onset of arrhythmia, or within the first two, three or four seconds after the onset of arrhythmia, when the efficacy of the therapeutic pulse is greater.

In a preferred embodiment, the step of delivering a second therapeutic electrical pulse is followed by the steps of: monitoring the effectiveness of the second therapeutic electrical pulse in treating the cardiac arrhythmia 5a, and then delivering a third therapeutic electrical pulse 6a to the heart of the patient if the second therapeutic electrical pulse is not effective in treating the arrhythmia. The third therapeutic electrical pulse can be a higher energy pulse than the second therapeutic electrical pulse, can be a different waveform, and/or can be across a different current path. Again, the third therapeutic pulse can be delivered from a storage capacitor, which may be the same or different from the storage capacitor employed to deliver the second therapeutic pulse. Charging of the storage capacitor, whether it is the same or different, may be initiated when the arrhythmia is first predicted and prior to the first therapeutic pulse, between the first and second therapeutic pulse, between the second and third therapeutic pulse, or combinations thereof. In this manner, the third therapeutic pulse may likewise be delivered promptly, within three or five seconds after the second therapeutic pulse. Cardiac therapy systems configured to carry out the method described above are described in detail below.

Figure 2:
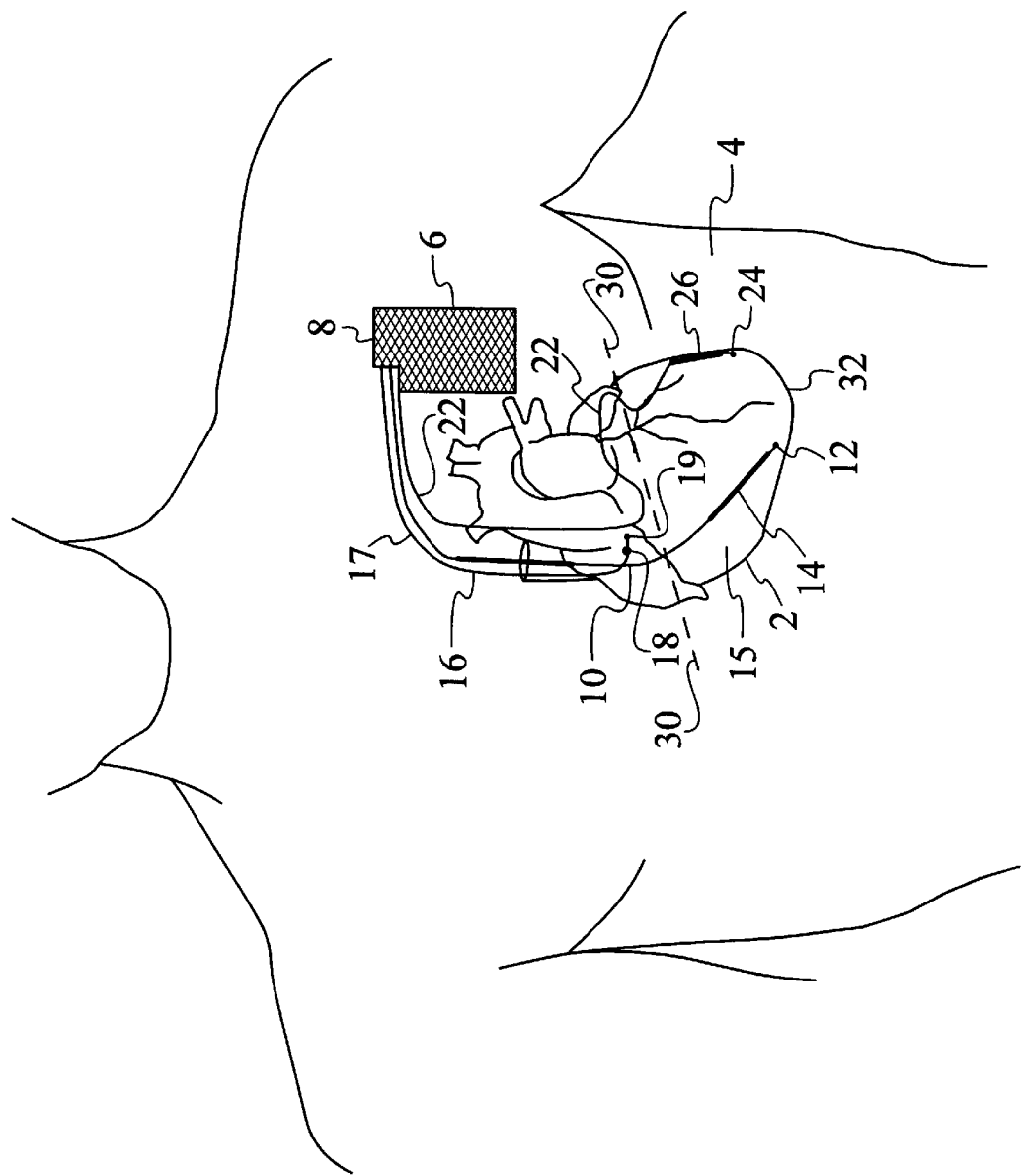
FIG. 2 illustrates an apparatus of the present invention, as implanted in the left pectoral region of a human subject and with electrodes positioned in the subject's heart.

Preferably, the left ventricle electrode is positioned within a vein traversing the lateral left ventricular free wall, midway between the base and apex of the heart (the base of the heart is identified by line 30–30' in FIG. 2; and the apex of the heart is identified by number 32 in FIG. 2). In general, depending on the particular heart anatomy, the vein is thus either the posterior cardiac vein or a tributary to the inferior cardiac vein. The electrode may be a solid electrode, because, in such small diameter veins, plugging of the vessel by the electrode is not deleterious to the patient because an alternative route of blood return around the blockage will be available.

The method of sensing electrical activations in the left ventricle (LV) myocardium from an electrode positioned in a coronary vein using an implanted device as described herein presents an opportunity to collect and utilize additional information not previously known. Such information derived from sensing the electrical activity of the LV permits improved rhythm classification and further, identification and subsequent classification of the origin of premature beats that commonly occur in ICD patients.

The effectiveness of ICD therapy is predicated on the accurate and precise classification of cardiac rhythm. The ICD continuously monitors a patients intrinsic heart rhythm. When the rhythm is classified as abnormal, the device may behave differently in comparison to times when the rhythm is normal. For example, if the intrinsic activation intervals sensed in the ventricle exceed some preset limit, a pacing pulse is issued. Still further, if the activation events are sensed in rapid succession that satisfy detection criteria, antitachycardia pacing or high voltage shocks may be delivered by the device to treat the arrhythmia. However, there are some cardiac rhythms which, while abnormally fast, might not be malignant. Examples of nonmalignant tachyarrhythmias include exercise induced sinus tachycardia and supraventricular tachycardia such as atrial flutter and atrial fibrillation.

The present invention can be carried out by utilizing the temporal sequence of activation times obtained from spatially disparate sites on the heart. The relative timing among activation events allows specific detection algorithms contained in the ICD to discriminate between rhythms that require immediate therapy and those rhythms for which therapy can be safely inhibited.

Method to Improve Sensitivity and Specificity of Rhythm Classification. FIG. 2 shows a human heart 2 residing within the thorax 4. An ICD pulse generator 6 is implanted under the skin in the infraclavicular area. Three separate leads exit the ICD header 8. Lead 10 is used for sensing electrical activity in the heart muscle and for delivery of electrical therapy to the heart. Electrode 12 (right ventricle 1; RV1) at the distal tip of lead 10 is used for pacing and sensing and is normally fabricated from a platinum material. Electrode coil 14 (right ventricle 2; RV2), mounted on lead 10, resides in the right ventricle 15 after implantation and provides an electrical discharge surface for delivery of high voltage shocks and for sensing electrical activity in the heart muscle. Electrode 16 (superior vena cava; SVC) also part of lead 10, serves as an electrical discharge surface for delivery of high voltage shocks and for sensing of electrical activity in the heart muscle. Lead 17 is an atrial lead for sensing and pacing in the right atrium 20. Electrode 18 (right atrium 2; RA2) is a ring electrode and electrode 19 (right atrium 1; RA1) is the pacing tip electrode of a standard atrial lead, known to those skilled in the art. Lead 22 is operatively connected to the ICD by header 8 and passes into the coronary sinus, into the cardiac vein and continues down a tributary, peripheral coronary vein such as the anterior interventricular vein, the posterior cardiac vein or the middle cardiac vein. An electrode 24 (left ventricle 2; LV2) can be used to pacing the heart and for sensing electrical activity, while electrode 26 (left ventricle 1; LV1) forms an electrical discharge surface for high voltage (>10 V) shocks.

Figure 3A:
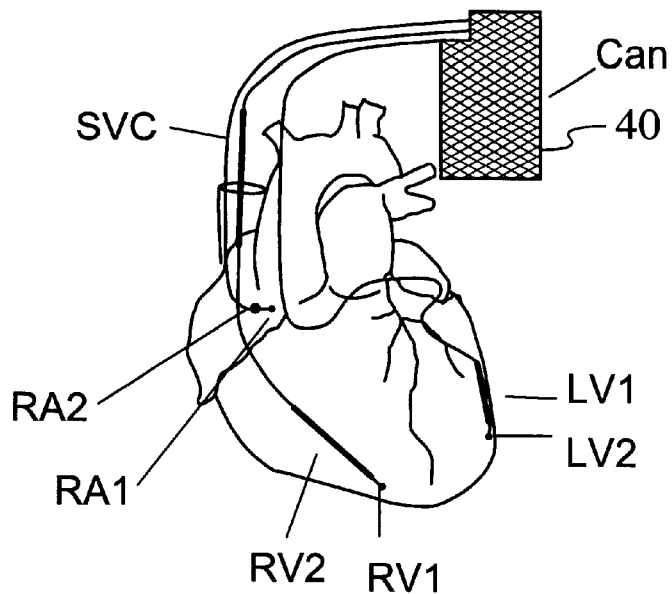
FIG. 3A illustrates an apparatus similar to that of FIG. 2.
Figure 3B:
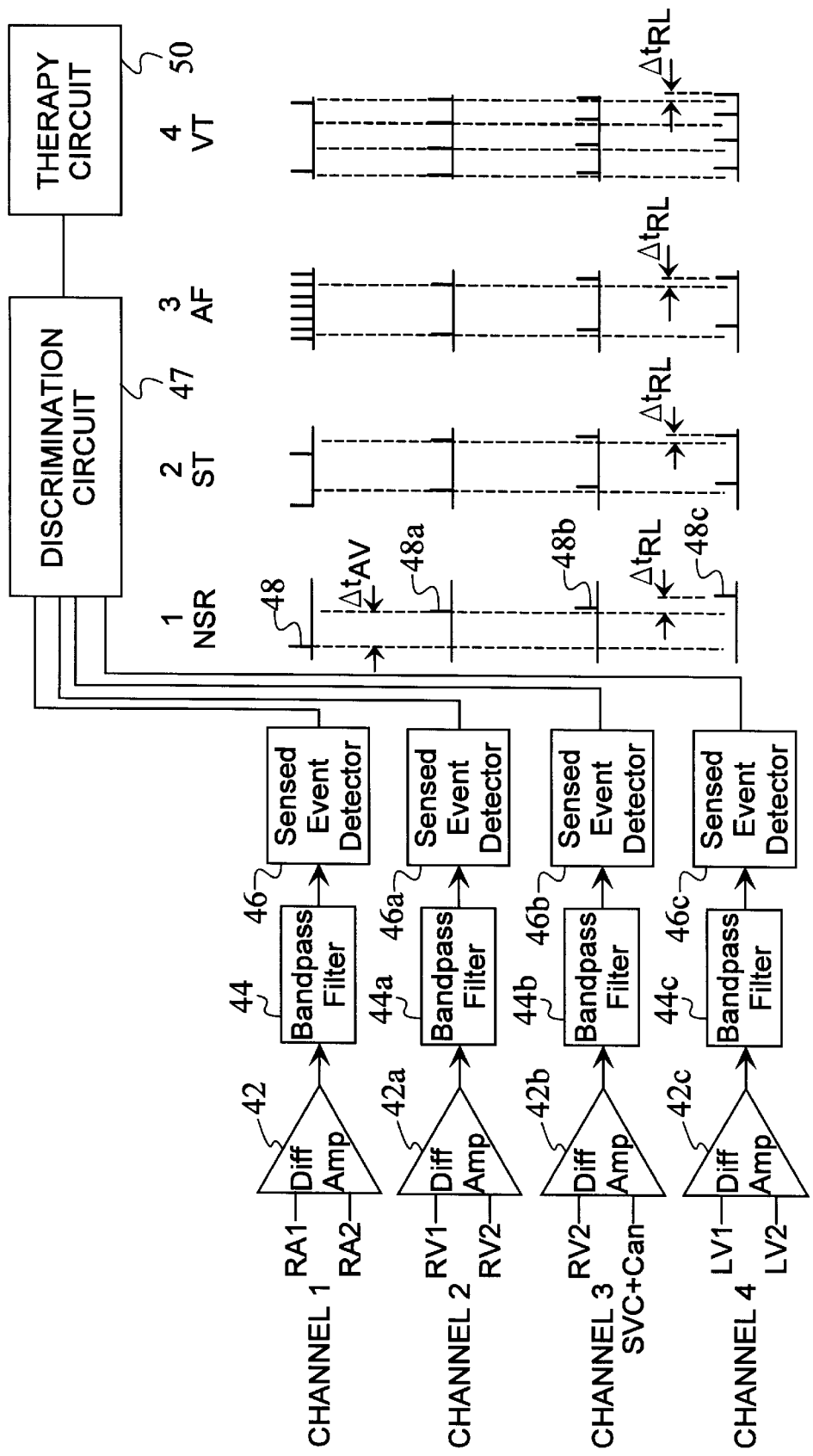
FIG. 3B illustrates the electrode connection and circuitry of an apparatus of FIG. 3A configured for detecting various types of medical conditions of the heart.

FIG. 3 shows, in panel A, an ICD 40 structurally configured essentially as described in FIG. 2. In panel B, the sensing configurations are shown. Hardware and sensed information are shown schematically, in rows, for each of channels 1 through 4. Electrograms for different electrode configurations are arranged in columns, with column 1 illustrating normal sinus rhythm, column 2 illustrating sinus tachycardia, column 3 illustrating atrial fibrillation, and column 4 illustrating ventricular tachycardia.

Electrodes shown in the positions illustrated panel 3A are, as shown in panel 3B, operatively connected to differential amplifiers 42, 42a, 42b, 42c, in turn connected to bandpass filters 44, 44a, 44b, 44c and sensed event detector circuitry 46, 46a, 46b, 46c, contained in the ICD 40. Amplification and bandpass filtering are followed by sensed event detection. The event that is sensed by detector 46–46c is preferably the local myocardial activation time. The preferred method for determining local activation time requires computation of the first temporal derivative of the extracellular electrogram (dV/dt). The local activation time using this method corresponds to the most negative value (minimum) of dV/dt. However, the present invention is not restricted to local activation times determined solely by dV/dt criteria. Less computationally intensive methods may be utilized in implanted devices. The activation time features may include, but not be limited to a local peak in the electrogram. With reference to the preferred embodiment, the sensed event occurs when a wave of activation passes near the sensing electrode. The potential difference between the electrodes is detected by the circuitry which issues an activation time marker 48, 48a, 48b, 48c (labeled in the NSR column only).

With continued reference to FIG. 3, The right panel right hand portion of panel B shows the temporal relationship among activation time markers for various rhythms, including normal sinus rhythm (NSR), sinus tachycardia (ST), atrial fibrillation (AF) and ventricular tachycardia (VT). The relative timing among the activation time markers provides a syntactic signature of the beat. During normal sinus rhythm there will exist a relationship between the activation time markers. Deviations from this normal syntactic signature may be detected by the ICD and used to discriminate among cardiac rhythms.

For normal sinus rhythm (NSR), an activation time marker first appears at the atrial electrode pair (RA1 and RA2). As the wave of electrical activity passes through the sinus node and activates the RV apex, an activation time marker is registered for the RV1, RV2 recording channel. The time difference between channels 1 and 2 is $\Delta t_{AV}$ and is composed of the intra-atrial conduction time, the AV nodal delay and the intraventricular conduction time. The time difference between activation markers on channels 2 and 4 is the interventricular conduction time ($\Delta t_{RL}$), were RL means right to left. Under normal conditions, the relative timing among these sensed events remains relatively unchanged. In the presence of abnormal rhythms, this temporal sequence of events will be altered compared to NSR.

Sinus tachycardia (ST) is a cardiac rhythm often associated with physical exertion. In the absence of AV nodal conduction abnormalities, the atrial activation intervals are equal to the ventricular activation intervals, although the absolute interval in the case of ST may be only 50% of the intervals observed during NSR. The present invention contemplates that the temporal relationships between sensed events will be very similar to those that exist during NSR. In contrast, the temporal sequence of events that are present during AF and VT are markedly different than during NSR.

Representative examples of the temporal sequence of sensed events for four different cardiac rhythms are shown in FIG. 3, panel B. As will be seen, these events can be readily distinguished by a discrimination circuit 47 operatively associated with the sensed event detector. Appropriate therapy can then be triggered by a therapy circuit 50 in accordance with known techniques, as discussed in greater detail below.

In an alternative embodiment of the present invention, the temporal sequence of sensed events is combined with information concerning the shape (morphology) of certain electrograms.

Method to Predict Spontaneous Arrhythmia Onset. Potentially lethal ventricular arrhythmias occur when waves of electrical activity sweep across the ventricles with a characteristic frequency that is higher than normal. The abnormally frequent activation cycles prevent the heart from supplying sufficient oxygenated blood to sustain the viability of vital organ systems (brain, liver, kidneys and the heart itself). The underlying causes for this abnormal cardiac electrical activity are varied. The propagation of normal electrical waves of activity may be transiently perturbed by sudden changes in the electrophysiological behavior of heart cells in specific regions of the heart. Such perturbations are known to occur in the presence of obstructed blood supply or abnormal activation of nerves leading into the heart muscle. Further, the onset of ventricular tachyarrhythmias frequently occur in the presence of electrical impulses that are appear abnormally in locations that are not consistent with normal rhythm. Such impulses are called ectopic impulses (not of SA node origin). When these ectopic impulses begin to propagate from their site of origin prior to the onset of the next normal heart beat, they are said to be "premature." Such ectopic beats occurring earlier than expected are called "premature ventricular activations." Ectopic beats occurring later than expected are delayed ventricular activations. When the ectopic ventricular activations result in a meaningful contractile response, they are termed ectopic ventricular contractions.

Localization of Ectopic Beat Origin. Ectopic beats have been linked to the initiation of atrial and ventricular tachyarrhythmias. Ectopic beats encounter regions of refractory tissue thereby establishing the electrophysiological conditions required for reentry, a mechanism of tachyarrhythmia. Ectopic beats occurring in the ventricles may arise from conducted atrial premature beats or from one or more ectopic foci residing in the ventricular muscle. Knowledge concerning the origin of ectopic beats increases the predictive accuracy of assessments related to the arrhythmogenicity of premature beats.

Figure 4A:
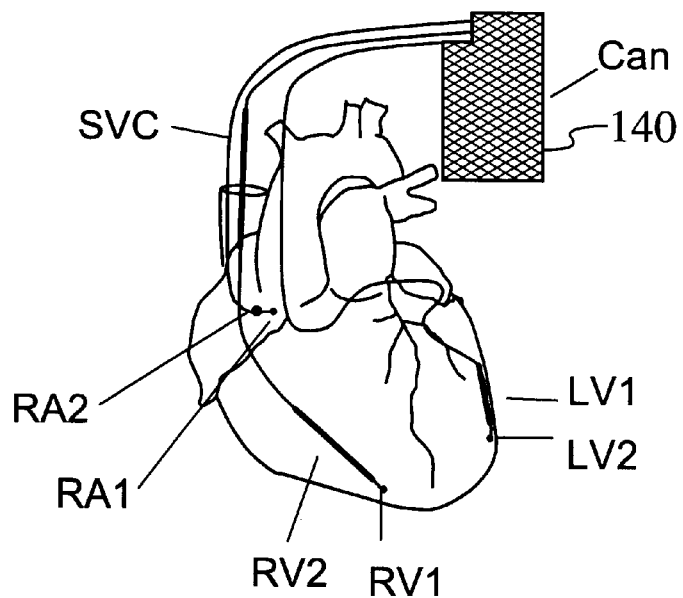
FIG. 4A illustrates an apparatus similar to that of FIG. 2.
Figure 4B:
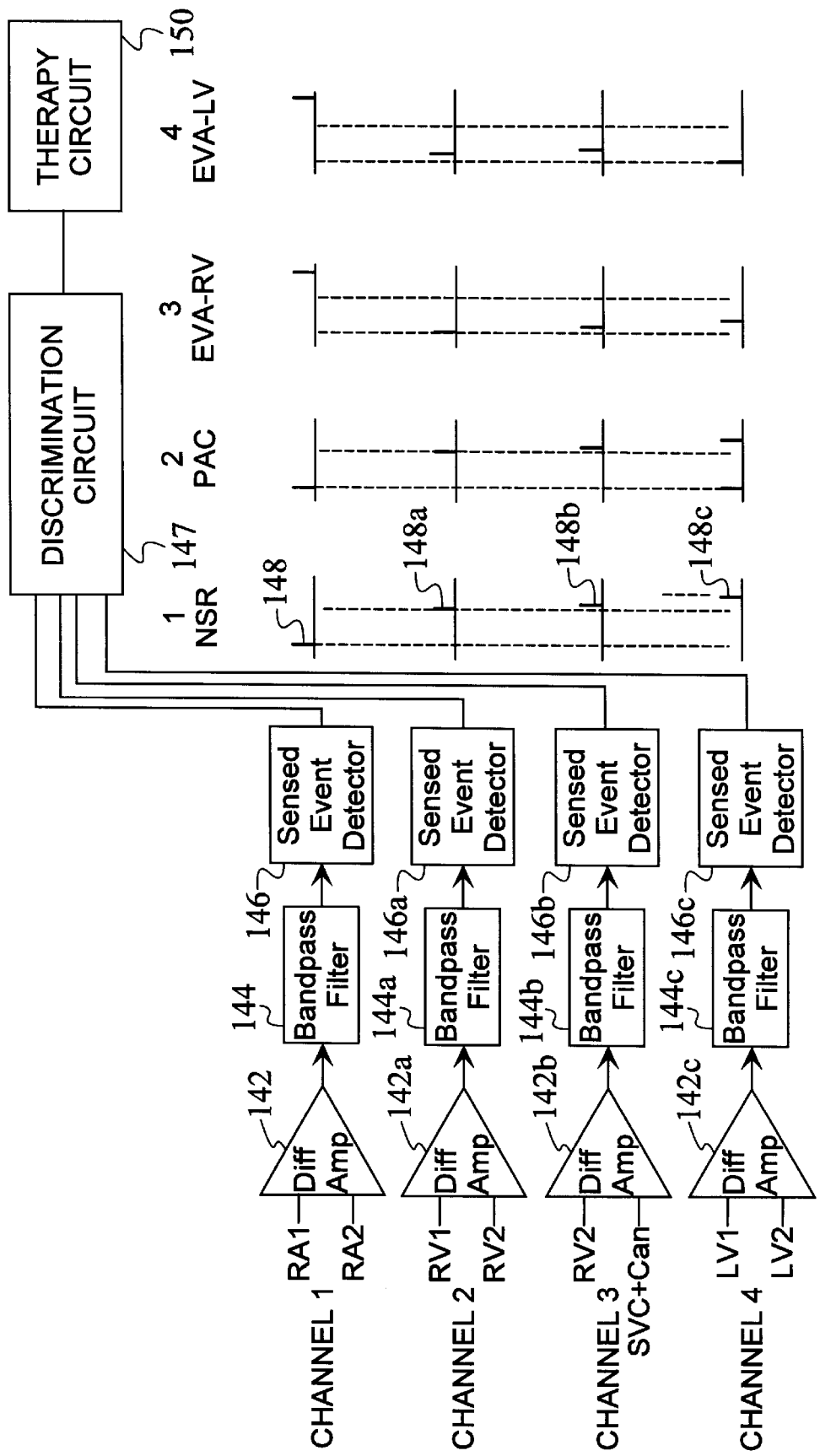
FIG. 4B illustrates the electrode connection and circuitry of an apparatus of FIG. 4A, configured for detecting premature beats and thereby predicting various medical conditions of the heart.

FIG. 4 is essentially the same as FIG. 3, except that it illustrates how an apparatus of the present invention can be employed so that the temporal sequence of sensed events permits determination of the origin of the premature beat. Panel 4A, shows an ICD 140 structurally configured essentially as described in FIG. 2. In panel 4B, the sensing configurations are shown. Hardware and sensed information are shown schematically, in rows, for each of channels 1 through 4. Electrograms for the different electrode configurations are arranged in columns, with column 1 illustrating normal sinus rhythm, column 2 illustrating ectopic atrial contraction (PAC), column 3 illustrating right ventricle ectopic ventricular activation (EVA-RV), and column 4 illustrating left ventricle ectopic ventricular activation (EVA-LV).

There are several benefits, not readily apparent, provided by the determination of the ectopic ventricular activation frequency and identification of the ectopic ventricular activation chamber of origin. First, the origin of premature ventricular activation is indicative of electrophysiological stability of the ventricles. Changes in the origin and frequency of ventricular ectopic activations thus indicates the onset of spontaneous ventricular tachyarrhythmia.

In order to predict the spontaneous onset of potentially lethal ventricular tachyarrhythmias, the electrophysiological status of the heart muscle must be monitored. A goal of this monitoring is to determine the frequency and location of ectopic ventricular activations (ectopic beats) and to determine the electrophysiological state of the heart in order to predict the likelihood that any one of the ectopic ventricular activations will yield a potentially lethal ventricular tachyarrhythmia.

The electrophysiological state of the heart can be characterized by analyzing characteristics of sensed electrical signals acquired by implanted devices containing appropriate amplifiers, filters and computational algorithms. During normal sinus rhythm an intrinsic electrical impulse spontaneously arises in the right atrium and is conducted to the ventricles through the atrio-ventricular node to the ventricles. Electrograms recorded from electrodes provide information about the conduction of the impulse and the repolarization of tissue. When the impulse traveling the heart muscle propagates near the sensing electrode, the amplitude of the signal changes, typically reaching a maximum as the impulse propagates closest to the sensing electrode. The moment at which the rate of change in the electrogram signal reaches a maximum is called the local activation time. By comparing the local activation times from several sensing electrodes located in different regions of the heart, a relationship between the activation times is established for normal heart rhythms. Each sensing site is connected to a separate sensing channel. The temporal sequence of activation times present among the various sensing channels forms a "syntactic signature" for the normal heart rhythm. When an ectopic ventricular activation is detected the temporal relationship among activation times will be altered. An algorithm is applied to the sensed activation times to determine the chamber from which the ectopic ventricular activation originated. The frequency and chamber origin of premature ventricular activations is tabulated by the device and reported to the physician during device interrogation by the physician.

Thus, different cardiac conditions can be predicted by discrimination circuit 147, and this information either downloaded from the device, or used to trigger a therapeutic treatment from ICD 140 by activation of a therapy circuit 150 contained therein.

Therapy systems. As noted above, the present invention provides for treatment of the diagnosed or prognosed medical condition of the heart. Thus, the system will further include a therapy circuit 50 or 150, as illustrated in FIGS. 3 and 4 above. Any suitable therapy circuit may be employed, including but not limited to those described in U.S. Pat. Nos. 5,282,837 to Adams, 5,433,729 to Adams, 5,014,696 to Mehra, 5,099,838 to Bardy, 5,431,683 to Bowald, and 5,690,686 to Min. In general, the therapy circuit comprises a plurality of primary electrodes (for example, various pairs of electrodes 16, 14, 26, and 6 (where electrode 6 refers to an active external portion of the housing)) configured for delivering a therapeutic pulse to the heart; a power supply (contained within the ICD); and a control circuit (contained within the ICD) operatively associated with the power supply, the primary electrodes and the predictor circuit, the control circuit configured for delivering a therapeutic pulse through the primary electrodes upon the prediction of future onset of cardiac arrhythmia in the patient. The discrimination circuit 47 or 147 as illustrated in FIGS. 3 and 4 serves as the prediction circuit. Preferably, one of the primary electrodes for the therapeutic pulse is configured for positioning through the coronary sinus ostium and within a vein on the surface of the left ventricle of the heart (e.g., electrode 26 in FIG. 2).

Figure 5:
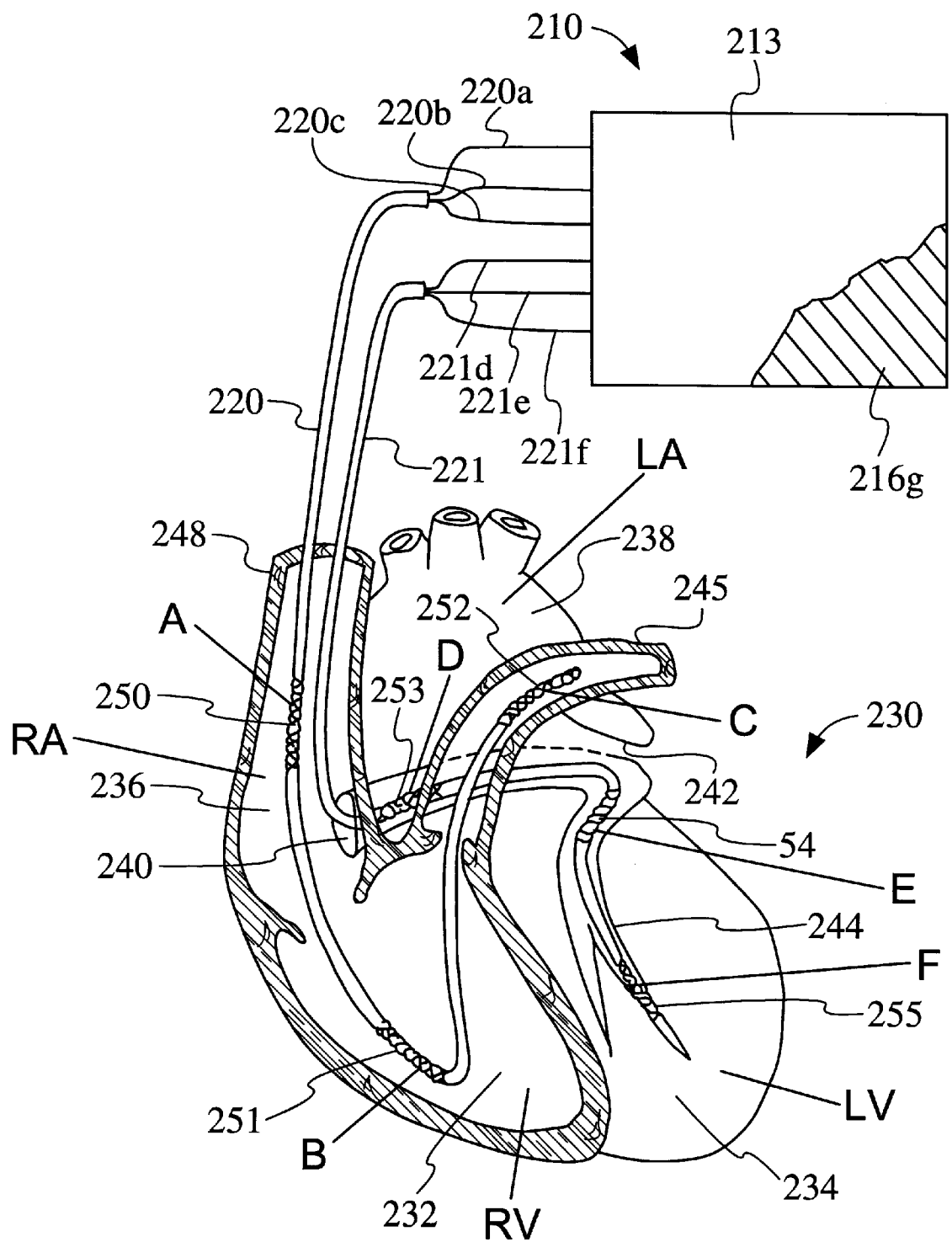
FIG. 5 schematically illustrates electrode placement for administering therapeutic electric treatments to the atria or ventricles in accordance with the present invention.

One preferred therapy system that can be used in practicing the present invention is illustrated in FIG. 5. The ICD device 210 of FIG. 5 includes an implantable housing 213 that contains a hermetically sealed electronic circuit 215. The housing optionally, but preferably, includes an electrode comprising an active external portion 216 of the housing, with the housing 213 preferably implanted in the left or right thoracic region of the patient (e.g., subcutaneously, in the left pectoral region) in accordance with known techniques as described in G. Bardy, U.S. Pat. No. 5,292,338. The system includes a first catheter 220 and a second catheter 221, both of which are insertable into the heart (typically through the superior or inferior vena cava) without the need for surgical incision into the heart. The term "catheter" as used herein includes "stylet" and is also used interchangeably with the term "lead". Each of the catheters 220, 221 contains electrode leads wires 220a, 220b, 220c, 221d, 221e, and 221f, respectively, with the small case letter designation corresponding to the large-case letter designation for the defibrillation electrode to which each lead wire is electrically connected.

As illustrated in FIG. 5, the catheter 20 includes an electrode A; 250 that resides in the right atrium (the term "right atrium" herein including the superior vena cava and innominate vein), an electrode B; 251 positioned in the right ventricle (preferably in the right ventricular apex), and an electrode C; 252 positioned within the left pulmonary artery (the term "left pulmonary artery" herein includes the main pulmonary artery and the right ventricular outflow tract).

The second catheter 221 includes, from proximal to distal, a first electrode D; 253 positioned in the proximal coronary sinus, adjacent the coronary sinus ostium or "os" 240; a second electrode E; 255 positioned in the distal coronary sinus (preferably as far distal in the coronary sinus as possible)(the term "distal coronary sinus" herein includes the great cardiac vein); and a third electrode F; 256 at or adjacent the tip of the catheter in a coronary vein on the surface (preferably the posterolateral surface) of the left ventricle (e.g., in the lateral-apical left ventricular free wall). The position of electrode F may be achieved by first engaging the coronary sinus with a guiding catheter through which a conventional guidewire is passed. The tip of the torqueable guidewire is advanced under fluoroscopic guidance to the desired location. The lead 221 on which electrode F is mounted passes over the guidewire to the proper location. The guidewire is withdrawn and electrode F is incorporated into the defibrillation lead system.

Electrode A, 252 may optionally be positioned on lead 221 and retain the same operable positions described above as when positioned on lead 220.

The active external portion of the housing 216 serves as an optional seventh electrode G, which may be used for either atrial or ventricular defibrillation.

The electrodes described in FIG. 5 and the specification above may, for convenience, be designated by the most adjacent structure. These structures are: the right atrium (RA), right ventricle (RV), pulmonary artery (PA), coronary sinus ostium (OS), distal coronary sinus (CS), and left ventricle (LV). Thus, when applied to electrodes the electrodes of FIG. 5:

RA means electrode A, 250;
RV means electrode B, 251;
PA means electrode C, 252;
OS means electrode D, 253;
CS means electrode E, 254; and
LV means electrode F, 255.

Figure 6:
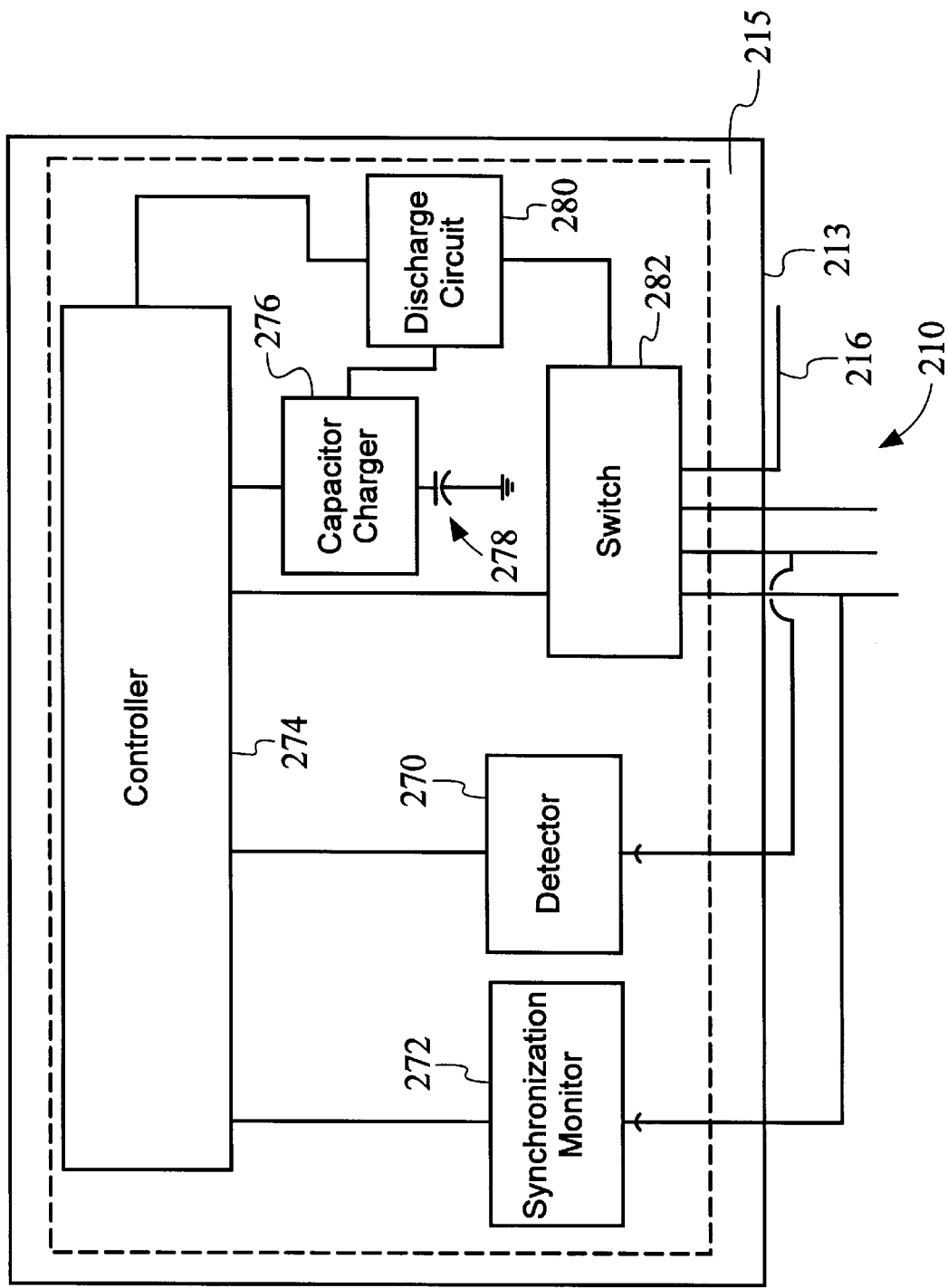
FIG. 6 schematically illustrates a circuit for carrying out the present invention.

FIG. 6 illustrates one example of an implantable housing 213 containing an electronic circuit 215, which includes one or more amplifiers (not shown) for amplifying sensed cardiac signals. The amplified signals are analyzed by detector 270 which determines if (or other arrhythmia, depending on the specific treatment for which the device is configured) is present, or is predicted to occur in the future (Preferably the amplifiers and detection circuitry are as described in FIGS. 3–4 above, which circuitry is presented in schematic form in FIG. 6 for simplicity). The detector 270 may be one of several known to those skilled in the art. As illustrated, a sensing signal may be provided by the electrode A 250, it will be appreciated by those of skill in the art that the sensing electrode may also be a plurality of sensing electrodes with a plurality of signals, such as bipolar configurations, and may also be electrodes that are positioned in alternate cardiac areas as is known in the art, such as for example, the CS. In this situation, the input line to the detector may be a plurality of lines which if providing only sensing will provide an input to the detector.

Ventricular sensing for timing the shocks for atrial defibrillation is performed from the RV and/or LV electrodes.

The therapy electrodes may alternately be configured to sense cardiac cycles, or may have smaller sensing electrodes placed adjacent thereto and thereby provide input to the electronics package as well as provide a predetermined stimulation shock output to predetermined cardiac areas as directed by the controller.

The electronic circuit 215 also includes a cardiac cycle monitor ("synchronization monitor 272") for providing synchronization information to the controller 274. As discussed below, the synchronization is typically provided by sensing cardiac activity in the RV, but may also include other sensing electrodes which can be combined with the defibrillation electrodes or employed separately to provide additional assurance that defibrillation shock pulses are not delivered during sensitive portions of the cardiac cycle so as to reduce the possibility of inducing ventricular fibrillation.

Upon a signal from the detector 270, the controller 274, in turn, signals a capacitor charging circuit 276 which then charges the storage capacitor 278 to a predetermined voltage, typically from a battery source (not shown). Initiation of charging of the capacitor can be in preparation for a therapy pulse that will be delivered, or may be in preparation for a therapy pulse that may or may not be delivered depending on subsequent monitoring of the heart after charging is initiated, as discussed above. The storage capacitor is typically 20 to 400 microfarads in size, and may be a single capacitor or a capacitor network (further, as discussed below, separate pulses can be driven by the same or different capacitors). The discharge of the capacitor is controlled by the controller 274 and/or a discharge circuit 280. The controller, based on information from the synchronization monitor 72, typically allows or directs the preselected shock pulse to be relayed to either a discharge circuit for further processing (i.e., to further shape the waveform signal, time the pulse, etc.) or directly to a switch. The controller may also control the proper selection of the predetermined defibrillation electrode pair(s), where multiple defibrillation electrodes are used, to direct the switch to electrically activate a desired electrode pair to align the predetermined electric shock pulse pathway through which the shock pulse is provided. As an alternative to a detector, the defibrillation pulses may be triggered by an external signal administered by a physician, with the physician monitoring the patient for the appropriate time of administration.

Numerous configurations of capacitor and control circuitry may be employed. The power supply may include a single capacitor, and the control circuit may be configured so that both the auxiliary pulse and the defibrillation pulse are generated by the discharge of the single capacitor. The power supply may include a first and second capacitor, with the control circuit configured so that the auxiliary pulse is generated by the discharge of the first capacitor and the defibrillation pulse is generated by the discharge of the second capacitor. In still another embodiment, the power supply includes a first and second capacitor, and the control circuit may be configured so that the auxiliary pulse is generated by the discharge (simultaneous or sequential) of both the first and second capacitors, and the defibrillation pulse likewise generated by the discharge of the first and second capacitors.

As illustrated by Table 1 below, numerous different combinations of electrodes from those shown in FIG. 5 may be employed to carry our atrial and ventricular defibrillation. In Table 1, polarity of electrode is illustrated by the direction of the arrows, but polarity is not critical and can be reversed. As will be seen from Table 1, a combination atrial and ventricular defibrillator may employ some or all of the electrodes illustrated in FIG. 5, and numerous combinations thereof.

TABLE 1

Electrode configurations.

|   | Ventricular Therapy pulse | Atrial Therapy pulse |
|---|---|---|
| 1 | RA->RV | RA->CS |
| 2 | RA->RV | PA->OS |
| 3 | RA->RV | RA->OS |
| 4 | RA->RV | OS->CS |
| 5 | RA->RV | CS->PA |
| 6* | RA->RV | PA->RA |
| 7 | PA->LV | RA->CS |
| 8 | PA->LV | PA->OS |
| 9 | PA->LV | RA->OS |
| 10 | PA->LV | OS->CS |
| 11 | PA->LV | CS->PA |
| 12 | PA->LV | PA->RA |
| 13 | RA->LV | RA->CS |
| 14 | RA->LV | PA->OS |
| 15 | RA->LV | RA->OS |
| 16 | RA->LV | OS->CS |
| 17 | RA->LV | CS->PA |
| 18 | RA->LV | PA->RA |
| 19 | PA->RV | RA->CS |
| 20 | PA->RV | PA->OS |
| 21 | PA->RV | RA->OS |
| 22 | PA->RV | OS->CS |
| 23 | PA->RV | CS->PA |
| 24* | PA->RV | PA->RA |
| 25 | RV->LV | RA->CS |
| 26 | RV->LV | PA->OS |
| 27 | RV->LV | RA->CS |
| 28 | RV->LV | OS->CS |

TABLE 1-continued

Electrode configurations.

| | Ventricular Therapy pulse | Atrial Therapy pulse |
|---|---|---|
| 29 | RV->LV | CS->PA |
| 30 | RV->LV | PA->RA |

Note that configurations 6 and 24, marked by an asterisk, employ Catheter A only.

Those skilled in the art will appreciate that still additional electrode combinations are possible for both atrial and ventricular defibrillation by employing the "active can" electrode G, 216, as discussed in greater detail below. In addition, multiple electrodes can be electrically coupled or "tied" together to form a single pole. For example, a shock can be delivered from either the RV or LV as one pole to the PA and OS tied together as the other pole.

Any suitable waveform may be used to carry out the present invention, including both monophasic and biphasic waveforms. Amplitude, polarity, and duration of waveforms are not critical and will be apparent to those skilled in the art, particularly in light of the further discussion below.

In a preferred embodiment of the invention, both atrial and ventricular defibrillation pulses are delivered along dual current pathways. Any combination of pathways among those set forth in Table 1 above may be employed. Particularly preferred current pathways employing the electrode configurations of FIG. 5 are set forth in Table 2 below.

TABLE 2

Dual current pathway electrode configurations.

| | Ventricular therapy pulse | | Atrial therapy pulse | |
|---|---|---|---|---|
| | Pulse segment 1 | Pulse segment 2 | Pulse segment 1 | Pulse segment 2 |
| 1 | RV->RA | LV->PA | LV->RA | RV->PA |
| 2 | RV->RA | LV->PA | LV->PA | RV->RA |
| 3 | RV->PA | LV->RA | LV->RA | RV->PA |
| 4 | RV->PA | LV->RA | LV->PA | RV->RA |
| 5 | RV->RA | LV->PA | RA->CS | PA->OS |
| 6 | RV->PA | LV->RA | RA->CS | PA->OS |

As in Table 1 above, polarity of electrodes is illustrated by the direction of the arrows, but polarity is not critical and can be reversed. In addition in Table 2, the order of pulse 1 and pulse 2 may be switched, both for atrial defibrillation and ventricular defibrillation.

When dual current pathways are employed for the defibrillation shock, the waveform for each current pathway may be monophasic or biphasic. The time between the first and second waveforms, will be apparent to those skilled in the art, but is preferably from 0 to 100 or 500 milliseconds, and more preferably from 0.1 to 50 milliseconds.

A. Atrial Therapy

In overview, an implantable system for the delivery of therapy pulses to the atria of a patient's heart comprises (a) a first pair of atrial defibrillation electrodes configured for delivering a first atrial therapy pulse along a first current pathway in the heart; (b) a pulse generator operatively associated with the first pair of atrial therapy electrodes for delivering the first atrial defibrillation pulse; (c) a second pair of atrial therapy electrodes configured for delivering a second atrial therapy pulse along a second current pathway in the heart, with the second current pathway different from the first current pathway; and (d) a pulse generator operatively associated with the second pair of atrial therapy electrodes for sequentially delivering the second atrial therapy pulse after the first therapy pulse. The electrode pairs may be placed in a variety of different locations, as long as different current pathways for the first and second pulse are thereby achieved. A single electrode may participate in more than one electrode pair, so that, for example, two current pathways are achieved through three therapy electrodes. Additional electrodes may be tied together to one member of an electrode pair to provide a single pole, if so desired, and additional electrodes may be provided for following the first and second shocks with additional shocks.

In one embodiment of the invention, the first pair of atrial therapy electrodes comprises a therapy electrode positioned in the right atrium or superior vena cava of the heart, and a therapy electrode positioned in the distal coronary sinus or great cardiac vein of the heart. The electrodes themselves may be configured for positioning in the indicated location. Numerous alternatives for the second pair of atrial therapy electrodes forming a second pathway are possible. For example, the second pair of atrial therapy electrodes may comprise:

(A) a therapy electrode positioned in the proximal coronary sinus of the heart, and a therapy electrode positioned anterior to the left atrium of the heart (e.g., in the left pulmonary artery or on the external surface of a device implanted subcutaneously in the left thoracic region of the patient):

(B) a therapy electrode positioned in the left pulmonary artery the heart, and a therapy electrode positioned in the right ventricle of the heart;

(C) a therapy electrode positioned in the distal coronary sinus or great cardiac vein of the heart, and a defibrillation electrode positioned in the right ventricle of the heart;

(D) a therapy electrode positioned in the left pulmonary artery of the heart, and a therapy electrode positioned in the right atrium of the heart;

(E) a therapy electrode positioned in the left pulmonary artery of the heart, and a therapy electrode positioned in the distal coronary sinus or great cardiac vein of the heart (the electrode positioned in the distal coronary sinus or great cardiac vein may optionally be tied together with an electrode positioned in the right atrium as one pole);

(F) a therapy electrode positioned in the proximal coronary sinus of the heart, and a therapy electrode positioned in the right atrium of the heart; or (G) a therapy electrode positioned in the proximal coronary sinus of the heart, and a therapy electrode positioned in the distal coronary sinus or great cardiac vein of the heart (the electrode positioned in the distal coronary sinus or great cardiac vein may optionally be tied together with an electrode positioned in the right atrium as one pole).

Again, the electrodes may be configured for positioning in the indicated locations, and numerous variations on the foregoing will be readily apparent to those skilled in the art. For example, the first therapy pulse could be delivered by the second pair of electrodes indicated above, and the second therapy pulse could be delivered by the first pair of electrodes indicated above (in which case the indicated second pair of electrodes serves as the "first pair" and the indicated first pair serves as the "second pair"). In addition, multiple electrodes may be implanted to provide three, four, or five or more different alternative electrode pairs and current paths, and the electrode coupling to the pulse generator switched after implantation of the electrodes to optimize the electrode configuration for a particular patient.

As noted above, the instant invention provides two separate shock pulses to two separate current pathways determined by the electrode pair arrangement also as discussed above. Therefore, it will be appreciated by those of skill in the art that the capacitor 278 may be a single capacitor or a bank of parallel capacitors sufficiently charged and sized to be able to provide at least two separate shock pulses to predetermined electrodes positioned in the heart. Additionally, the capacitor 278 can be two or more separately charged capacitors (or bank of parallel capacitors) on separate lines to provide two separate and sequential shock pulses as controlled by the controller 274 and/or the discharge circuit 280. However, it is preferred that the capacitor 278 be a relatively large capacitor for insuring sufficient charge and decay period (i.e., long time constant and low tilt) to provide sufficient energy for two shock pulses. For example, a capacitor with capacitance in the range of 200–1000 $\mu f$ or more, having an associated time constant in the range of 30 ms, would typically be charged to approximately 100–200 volts and would deliver a V(peak) in a typical first waveform of about 50–100 volts leading edge. If additional shocks beyond two are administered, then a larger capacitor may be employed. In the alternative wherein the electronic package employs a circuit to further shape the waveform, the capacitor may be charged to a higher voltage range (such as around 200 V).

In one embodiment of the invention, the pulse generator includes a single capacitor 278, and the controller 274 includes a switch (e.g., a crosspoint switch) operatively associated with that capacitor. The switch is configured to provide a biphasic pulse (i.e., a first phase of a pulse of a predetermined polarity followed by a second phase of a pulse of reversed polarity) as the first atrial defibrillation pulse and a biphasic pulse as the second atrial defibrillation pulse.

The controller 274 delivers a preselected electrical pulse to predetermined electrode pairs through a switch 282 which is preferably programmable. The capacitor charger 276, capacitor 278, controller 274, discharge circuit 280 and switch 282 thus form an electrical pulse generator. Therefore, it will be appreciated that in operation, in response to an input from the detector 270, the controller 274 controls the pulse generator to synchronize the delivery of the timed pulse output to the proper electrode pair in accordance with the cardiac cycle information received from the synchronization monitor 272 and the specific electrode configuration employed by the device. Further, when employing a biphasic waveform, it will be appreciated by those of skill in the art that the pulse generator also includes a crosspoint switch to switch the polarity of the electrode pair for delivery of the second (inverted or negative) waveform phase. It is also preferable that the electronic package include a receiver/transmitter coupled to the internal controller 274 for communicating with an external controller. Thus the pulse regimen could be altered by external input to the controller to alter for example, the waveform, the voltage, the electrode coupling, or even to retrieve data monitoring data received and stored in memory about the number of atrial fibrillation episodes and the effectiveness of the shock level.

In one embodiment of the invention, the switch 282 is programmable (e.g., by remote control such as by a radio signal) to alter the coupling of the pulse generator to the atrial defibrillation electrodes. This feature is advantageously employed when multiple electrodes are implanted so that the electrode pairs that deliver the first and second atrial defibrillation pulses may be changed to optimize the technique for a particular patient.

The energy of the first atrial defibrillation pulse is preferably not greater than 8 joules, more preferably not greater than 6 joules, still more preferably not greater than 4 joules, and most preferably not greater than 2 joules. The energy of the second atrial defibrillation pulse is typically not greater than the energy of the first defibrillation pulse (although such a result is possible where a dual capacitor design is employed), and is preferably not greater than 8 joules, more preferably not greater than 6 joules, still more preferably not greater than 4 joules, and most preferably not greater than 2 joules. The second atrial defibrillation pulse preferably follows the first atrial defibrillation pulse by 0 to 500 milliseconds, and more preferably follows the first atrial defibrillation pulse by 0 to 200 milliseconds. In the alternative, the second atrial defibrillation pulse may overlap the first atrial defibrillation pulse, for example by from one fourth to three fourths of the total shock duration (the duration of both shocks in series). The duration of each shock may be, for example, from three to twenty milliseconds, with total shock duration being, for example, from four and one half to forty milliseconds.

B. Ventricular Therapy

Another embodiment of the foregoing apparatus is an implantable system for the therapeutic treatment of the ventricles of the heart of a patient in need of such treatment. The system comprises a plurality of primary electrodes, at least one auxiliary electrode, a power supply, and a control circuit. The plurality of primary electrodes are configured for delivering a therapy pulse along a predetermined current pathway in a first portion of the heart, the current pathway defining a weak field area in a second portion of the heart. At least one auxiliary electrode is configured for delivering an auxiliary pulse to the weak field area, with the at least one auxiliary electrode configured for positioning through the coronary sinus and in a vein on the surface of the left ventricle of the heart. The control circuit is operatively associated with the primary electrodes, the at least one auxiliary electrode, and the power supply, the control circuit configured for delivering a cardioversion sequence comprising a monophasic auxiliary pulse through the auxiliary electrode, followed by a biphasic therapy pulse through the primary electrodes, with the therapy pulse delivered within 20 milliseconds after the auxiliary pulse, and with the first phase of the therapy pulse in opposite polarity to the auxiliary pulse.

The auxiliary pulse may be from 0.5 or 1 to 5 or 10 milliseconds in duration, with a 2 millisecond pulse currently preferred. The time interval from the end of the auxiliary pulse to the leading edge of the primary pulse may be from 1 or 2 milliseconds to 10, 15 or 20 milliseconds, with a delay of about 5 milliseconds currently preferred.

The optimal auxiliary-to-primary interval may differ depending on the type of rhythm or condition of the myocardial tissue at the time the therapy is applied. Therefore, the control circuitry may also be configured to sense a characteristic of the cardiac rhythm (e.g., an activation interval or a dynamical pattern of consecutive activation intervals) and then select an optimum auxiliary-to-primary shock time interval (e.g., from a look up table stored in a microprocessor memory).

In general, the control circuit is configured so that the auxiliary pulse is not more than 40% or 50% of the peak current and not more than 20% or 30% of the delivered energy (in Joules) of the therapy pulse. In a preferred embodiment, the trailing edge voltage of the auxiliary pulse is approximately or about equal to the leading edge voltage of the therapy pulse. Particular voltage, current, and energy outputs will depend upon factors such as the condition of the tissue and the particular disorder being treated. In general, the auxiliary pulse may have a peak voltage of from 20 or 30 volts to 200 or 250 volts, with a peak voltage range of 50 to 150 volts preferred. The energy of the auxiliary pulse may be from 0.01 or 0.05 to 1 or 2 Joules. The energy of the therapy pulse may be from 5 or 10 Joules to 30, 40 or 50 Joules.

C. Combined Atrial and Ventricular Therapy

While atrial and ventricular therapy systems are described separately above, a particularly preferred embodiment combines the two systems in a single method and apparatus. The detector 270 include is configured to detect whether atrial or ventricular therapy is indicated (e.g., by detecting the chamber of premature beat origin as described above, or in accordance with known techniques), and controller 274 and switch 278 are configured to deliver atrial or ventricular therapy as described above.

The foregoing is illustrative of the present invention, and is not to be construed as limiting thereof. Numerous additional features can be added to the instant invention. For example, the electrophysiological status of the heart muscle can be determined for each cardiac activation cycle (beat), or may be determined intermittently, the measurements being made only during select times separated by periods during which no measurements are made. Analyses can be simultaneously done on features extracted from electrograms that relate to the conduction of an impulse and features that relate to the recovery (repolarization) of heart tissue. Features related to the conduction of an impulse may be the width of a local electrogram and absolute time differences between sensed events at spatially disparate sensing sites throughout the heart. Features related to conduction may be conduction intervals of intrinsic or paced impulses determined by computing the time difference between sensed events obtained from sensing electrodes positioned in the right atrium, the right ventricle, and in a vein on the surface of the left ventricle. The dynamical behavior of the conduction intervals may be monitored. Accordingly, the invention is defined by the following claims, with equivalents of the claims to be included therein.

That which is claimed is:

1. A method of selecting a cardiac therapy to be delivered to a patient's heart for the prevention or treatment of cardiac arrhythmia by an implantable system said method comprising:

detecting electrical activity from the heart of said patient;
   predicting the future onset of a cardiac arrhythmia in said patient from said detected electrical activity;
   delivering a first therapeutic electrical pulse to the heart of said patient prior to the onset of cardiac arrhythmia; then
   monitoring the effectiveness of said first therapeutic electrical pulse in preventing cardiac arrhythmia from said detected electrical activity;
   delivering a second therapeutic electrical pulse to the heart of said patient at the onset of cardiac arrhythmia if said first therapeutic electrical pulse is not effective;
   monitoring the effectiveness of said second therapeutic electrical pulse in treating said cardiac arrhythmia; and then
   delivering a third therapeutic electrical pulse to the heart of said patient if said second therapeutic electrical pulse is not effective in treating said arrhythmia, said third therapeutic electrical pulse being a higher energy pulse than said second therapeutic electrical pulse.

2. A method according to claim 1, wherein said first and second therapeutic pulses are ventricular therapeutic pulses.

3. A method according to claim 1, wherein said step of delivering a first therapeutic electrical pulse is carried out with a plurality of primary electrodes;

a first one of said primary electrodes positioned through the coronary sinus ostium and within a vein on the surface of the left ventricle of said heart.

4. A method according to claim 1, wherein said step of delivering a second therapeutic electrical pulse is carried out with a plurality of primary electrodes;

a first one of said primary electrodes positioned through the coronary sinus ostium and within a vein on the surface of the left ventricle of said heart.

5. A method according to claim 1, wherein said step of delivering a third therapeutic electrical pulse is carried out with a plurality of primary electrodes;

a first one of said primary electrodes positioned through the coronary sinus ostium and within a vein on the surface of the left ventricle of said heart.

6. A method of selecting a cardiac therapy to be delivered to a patient's heart for the prevention or treatment of cardiac arrhythmia by an implantable system, said method comprising:

detecting electrical activity from the heart of said patient;
   predicting the future onset of a cardiac arrhythmia in said patient from said detected electrical activity;
   delivering a first therapeutic electrical pulse to the heart of said patient prior to the onset of cardiac arrhythmia; then
   monitoring the effectiveness of said first therapeutic electrical pulse in preventing cardiac arrhythmia from said detected electrical activity; and
   delivering a second therapeutic electrical pulse to the heart of said patient at the onset of cardiac arrhythmia if said first therapeutic electrical pulse is not effective;
   wherein said step of delivering a second therapeutic electrical pulse is carried out during the first three beats of cardiac arrhythmia.

7. A method of selecting a cardiac therapy to be delivered to a patient's heart for the prevention or treatment of cardiac arrhythmia by an implantable system said method comprising:

detecting electrical activity from the heart of said patient;
   predicting the future onset of a cardiac arrhythmia in said patient from said detected electrical activity;
   delivering a first therapeutic electrical pulse to the heart of said patient prior to the onset of cardiac arrhythmia; then
   monitoring the effectiveness of said first therapeutic electrical pulse in preventing cardiac arrhythmia from said detected electrical activity; and
   delivering a second therapeutic electrical pulse to the heart of said patient at the onset of cardiac arrhythmia if said first therapeutic electrical pulse is not effective;
   wherein said step of delivering a second therapeutic electrical pulse is carried out within the first three seconds of cardiac arrhythmia.

8. A method of selecting a cardiac therapy to be delivered to a patient's heart for the prevention or treatment of cardiac arrhythmia by an implantable system, said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity; and delivering a second therapeutic electrical pulse to the heart of said patient at the onset of cardiac arrhythmia if said first therapeutic electrical pulse is not effective;

wherein said step of detecting electrical activity from the heart is carried out with at least a first sensing electrode positioned within a vein on the left surface of the left ventricle of said heart.

9. A method according to claim 8, wherein said step of detecting electrical activity from the heart is further carried out with a second sensing electrode positioned within the right ventricle of said heart.

10. A method according to claim 9, wherein said step of detecting electrical activity from the heart is further carried out with a third sensing electrode positioned in the right atrium or superior vena cava of said heart.

11. A method of selecting a cardiac therapy to be delivered to a patient's heart for the prevention or treatment of cardiac arrhythmia by an implantable system said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity; and delivering a second therapeutic electrical pulse to the heart of said patient at the onset of cardiac arrhythmia if said first therapeutic electrical pulse is not effective;

wherein said detecting step is carried out by detecting premature beats in said heart; and wherein said detecting step further comprises the step of identifying the heart chamber of premature beat origin in said heart.

12. A method of selecting a cardiac therapy to be delivered to a patient's heart for the prevention or treatment of cardiac arrhythmia by an implantable system, said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity; and delivering a second therapeutic electrical pulse to the heart of said patient at the onset of cardiac arrhythmia if said first therapeutic electrical pulse is not effective;

wherein said detecting step comprises detecting the presence of sinus rhythm with syntactic relationships among electrogram features.

13. A method of selecting a cardiac therapy to be delivered to a patient's heart for the prevention or treatment of cardiac arrhythmia by an implantable system, said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity; and delivering a second therapeutic electrical pulse to the heart of said patient at the onset of cardiac arrhythmia if said first therapeutic electrical pulse is not effective;

wherein said detecting step further comprises the step of discriminating the location of origin of premature beats in said heart.

14. A method according to claim 13, wherein said discriminating step comprises discriminating an atrial location of origin from a ventricular location of origin of premature beats in said heart.

15. A method of selecting a cardiac therapy to be delivered to a patient's heart for the prevention or treatment of cardiac arrhythmia by an implantable system said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity;

delivering a second therapeutic electrical pulse to the heart of said patient at the onset of cardiac arrhythmia if said first therapeutic electrical pulse is not effective; and selecting an atrial or ventricular therapeutic electrical pulse as said first therapeutic electrical pulse based on said detected electrical activity.

16. A method of selecting a cardiac therapy to be delivered to a patient's heart for the prevention or treatment of cardiac arrhythmia by an implantable system, said method comprising:

detecting electrical activity from the heart of said patient;

predicting the future onset of a cardiac arrhythmia in said patient from said detected electrical activity;

delivering a first therapeutic electrical pulse to the heart of said patient prior to the onset of cardiac arrhythmia; then monitoring the effectiveness of said first therapeutic electrical pulse in preventing cardiac arrhythmia from said detected electrical activity; and delivering a second therapeutic electrical pulse to the heart of said patient at the onset of cardiac arrhythmia if said first therapeutic electrical pulse is not effective;

wherein said first and second therapeutic pulses are atrial therapeutic pulses.

17. An implantable system for selecting a cardiac therapy to be delivered to a patient's heart for the prevention or treatment of cardiac arrhythmia, said system comprising:
   a detector for detecting electrical activity from the heart of said patient;
   a discrimination circuit for predicting the future onset of a cardiac arrhythmia in said patient from said detected electrical activity; and
   a therapy circuit configured to deliver a first therapeutic electrical pulse to the heart of said patient prior to the onset of cardiac arrhythmia;
   said discrimination circuit further configured to monitor the effectiveness of said first therapeutic electrical pulse in preventing cardiac arrhythmia from said detected electrical activity;
   said therapy circuit further configured to deliver a second therapeutic electrical pulse to the heart of said patient at the onset of cardiac arrhythmia if said first therapeutic electrical pulse is not effective;
   wherein said discrimination circuit is further configured to monitor the effectiveness of said second therapeutic electrical pulse in treating said cardiac arrhythmia;
   and wherein said therapy circuit is configured to deliver a third therapeutic electrical pulse to the heart of said patient if said second therapeutic electrical pulse is not effective in treating said arrhythmia, said third therapeutic electrical pulse being a higher energy pulse than said second therapeutic electrical pulse.

18. A system according to claim 17, wherein said therapy circuit is configured to deliver ventricular therapy pulses as said first and second therapeutic pulses.

19. A system according to claim 17, further comprising a plurality of primary electrodes operatively associated with said therapy circuit for delivering said first therapeutic electrical pulse;
   a first one of said primary electrodes positioned through the coronary sinus ostium and within a vein on the surface of the left ventricle of said heart.

20. A system according to claim 17, further comprising a plurality of primary electrodes operatively associated with said therapy circuit for delivering said second therapeutic electrical pulse;
   a first one of said primary electrodes positioned through the coronary sinus ostium and within a vein on the surface of the left ventricle of said heart.

21. A system according to claim 17, further comprising a plurality of primary electrodes operatively associated with said therapy circuit for delivering said third therapeutic electrical pulse;
   a first one of said primary electrodes positioned through the coronary sinus ostium and within a vein on the surface of the left ventricle of said heart.

22. An implantable system for selecting a cardiac therapy to be delivered to a patient's heart for the prevention or treatment of cardiac arrhythmia, said system comprising:
   a detector for detecting electrical activity from the heart of said patient;
   a discrimination circuit for predicting the future onset of a cardiac arrhythmia in said patient from said detected electrical activity; and
   a therapy circuit configured to deliver a first therapeutic electrical pulse to the heart of said patient prior to the onset of cardiac arrhythmia;
   said discrimination circuit further configured to monitor the effectiveness of said first therapeutic electrical pulse in preventing cardiac arrhythmia from said detected electrical activity;
   said therapy circuit further configured to deliver a second therapeutic electrical pulse to the heart of said patient at the onset of cardiac arrhythmia if said first therapeutic electrical pulse is not effective and during the first three beats of cardiac arrhythmia.

23. An implantable system for selecting a cardiac therapy to be delivered to a patient's heart for the prevention or treatment of cardiac arrhythmia, said system comprising:
   a detector for detecting electrical activity from the heart of said patient;
   a discrimination circuit for predicting the future onset of a cardiac arrhythmia in said patient from said detected electrical activity;
   a therapy circuit configured to deliver a first therapeutic electrical pulse to the heart of said patient prior to the onset of cardiac arrhythmia;
   said discrimination circuit further configured to monitor the effectiveness of said first therapeutic electrical pulse in preventing cardiac arrhythmia from said detected electrical activity;
   said therapy circuit further configured to deliver a second therapeutic electrical pulse to the heart of said patient at the onset of cardiac arrhythmia if said first therapeutic electrical pulse is not effective within the first three seconds of cardiac arrhythmia.

24. An implantable system for selecting a cardiac therapy to be delivered to a patient's heart for the prevention or treatment of cardiac arrhythmia, said system comprising:
   a detector for detecting electrical activity from the heart of said patient;
   a discrimination circuit for predicting the future onset of a cardiac arrhythmia in said patient from said detected electrical activity; and
   a therapy circuit configured to deliver a first therapeutic electrical pulse to the heart of said patient prior to the onset of cardiac arrhythmia;
   said discrimination circuit further configured to monitor the effectiveness of said first therapeutic electrical pulse in preventing cardiac arrhythmia from said detected electrical activity;
   said therapy circuit further configured to deliver a second therapeutic electrical pulse to the heart of said patient at the onset of cardiac arrhythmia if said first therapeutic electrical pulse is not effective;
   said system further comprising at least a first sensing electrode configured for positioning within a vein on the left surface of the left ventricle of said heart operatively associated with said detector for detecting electrical activity from the heart.

25. A system according to claim 24, further comprising a second sensing electrode configured for positioning within the right ventricle of said heart and operatively associated with said detector for detecting electrical activity from the heart.

26. A system according to claim 25, further comprising a third sensing electrode positioned in the right atrium or superior vena cava of said heart and operatively associated with said detector for detecting electrical activity from the heart.

27. An implantable system for selecting a cardiac therapy to be delivered to a patient's heart for the prevention or treatment of cardiac arrhythmia, said system comprising:
   a detector for detecting electrical activity from the heart of said patient;

a discrimination circuit for predicting the future onset of a cardiac arrhythmia in said patient from said detected electrical activity; and a therapy circuit configured to deliver a first therapeutic electrical pulse to the heart of said patient prior to the onset of cardiac arrhythmia;

said discrimination circuit further configured to monitor the effectiveness of said first therapeutic electrical pulse in preventing cardiac arrhythmia from said detected electrical activity;

said therapy circuit further configured to deliver a second therapeutic electrical pulse to the heart of said patient at the onset of cardiac arrhythmia if said first therapeutic electrical pulse is not effective;

said discrimination circuit configured to detect detecting premature beats in said heart and to identify the heart chamber of premature beat origin in said heart.

28. An implantable system for selecting a cardiac therapy to be delivered to a patient's heart for the prevention or treatment of cardiac arrhythmia, said system comprising:

a detector for detecting electrical activity from the heart of said patient;

a discrimination circuit for predicting the future onset of a cardiac arrhythmia in said patient from said detected electrical activity; and a therapy circuit configured to deliver a first therapeutic electrical pulse to the heart of said patient prior to the onset of cardiac arrhythmia;

said discrimination circuit further configured to monitor the effectiveness of said first therapeutic electrical pulse in preventing cardiac arrhythmia from said detected electrical activity;

said therapy circuit further configured to deliver a second therapeutic electrical pulse to the heart of said patient at the onset of cardiac arrhythmia if said first therapeutic electrical pulse is not effective;

said discrimination circuit configured to detect the presence of sinus rhythm with syntactic relationships among electrogram features.

29. An implantable system for selecting a cardiac therapy to be delivered to a patient's heart for the prevention or treatment of cardiac arrhythmia, said system comprising:

a detector for detecting electrical activity from the heart of said patient;

a discrimination circuit for predicting the future onset of a cardiac arrhythmia in said patient from said detected electrical activity; and a therapy circuit configured to deliver a first therapeutic electrical pulse to the heart of said patient prior to the onset of cardiac arrhythmia;

said discrimination circuit further configured to monitor the effectiveness of said first therapeutic electrical pulse in preventing cardiac arrhythmia from said detected electrical activity;

said therapy circuit further configured to deliver a second therapeutic electrical pulse to the heart of said patient at the onset of cardiac arrhythmia if said first therapeutic electrical pulse is not effective;

said discrimination circuit further configured to discriminate the location of origin of premature beats in said heart.

30. A system according to claim 29, said discrimination circuit further configured to discriminate an atrial location of origin from a ventricular location of origin of premature beats in said heart.

31. An implantable system for selecting a cardiac therapy to be delivered to a patient's heart for the prevention or treatment of cardiac arrhythmia, said system comprising:

a detector for detecting electrical activity from the heart of said patient;

a discrimination circuit for predicting the future onset of a cardiac arrhythmia in said patient from said detected electrical activity;

a therapy circuit configured to deliver a first therapeutic electrical pulse to the heart of said patient prior to the onset of cardiac arrhythmia;

said discrimination circuit further configured to monitor the effectiveness of said first therapeutic electrical pulse in preventing cardiac arrhythmia from said detected electrical activity;

said therapy circuit further configured to deliver a second therapeutic electrical pulse to the heart of said patient at the onset of cardiac arrhythmia if said first therapeutic electrical pulse is not effective;

said discrimination circuit further configured to select an atrial or ventricular therapeutic electrical pulse as said first therapeutic electrical pulse based on said detected electrical activity.

32. An implantable system for selecting a cardiac therapy to be delivered to a patient's heart for the prevention or treatment of cardiac arrhythmia, said system comprising:

a detector for detecting electrical activity from the heart of said patient;

a discrimination circuit for predicting the future onset of a cardiac arrhythmia in said patient from said detected electrical activity;

a therapy circuit configured to deliver a first therapeutic electrical pulse to the heart of said patient prior to the onset of cardiac arrhythmia;

said discrimination circuit further configured to monitor the effectiveness of said first therapeutic electrical pulse in preventing cardiac arrhythmia from said detected electrical activity;

said therapy circuit further configured to deliver a second therapeutic electrical pulse to the heart of said patient at the onset of cardiac arrhythmia if said first therapeutic electrical pulse is not effective and to deliver atrial therapeutic pulses as said first and second therapeutic pulses.

* * * * *